United States Patent [19]

Bartmann et al.

[11] Patent Number: 5,118,848
[45] Date of Patent: Jun. 2, 1992

[54] PROCESS FOR THE PREPARATION OF 4,4'-BIS(4-AMINOPHENOXY)-DIPHENYL SULFONE

[75] Inventors: Martin Bartmann, Recklinghausen; Jürgen Finke, Marl; Wilfred Ribbing, Heesternweg; Günter Poll, Marl, all of Fed. Rep. of Germany

[73] Assignee: Huels Aktiengesellschaft, Marl, Fed. Rep. of Germany

[21] Appl. No.: 635,021

[22] Filed: Dec. 28, 1990

[30] Foreign Application Priority Data

Jan. 23, 1990 [DE] Fed. Rep. of Germany ....... 4001821

[51] Int. Cl.$^5$ ................. C07C 213/06; C07C 215/76; C07C 217/90
[52] U.S. Cl. .................................................... 564/430
[58] Field of Search ......................................... 564/430

[56] References Cited

FOREIGN PATENT DOCUMENTS 0021364 2/1982 Japan .
0021365 2/1982 Japan .
 113149 5/1989 Japan .

*Primary Examiner*—Marianne Cintins
*Assistant Examiner*—John D. Peabody
*Attorney, Agent, or Firm*—Millen, White & Zelano

[57] ABSTRACT

High purity 4,4'-bis(4-aminophenoxy)diphenyl sulfone is prepared from p-aminophenol, alkali metal hydroxide and 4,4'-dihalodiphenyl sulfone by using a molar ratio of alkali metal hydroxide: 4-aminophenol in the range of 1.0–1.1:1.0 and a molar ratio of 4-aminophenol: 4,4'-dihalodiphenyl sulfone in the range of 2.005–2.05:1.0 and by using a dialkylamide or N-alkyl lactam as a solvent. Pristine products (no-recrystallization) of 99.0% purity having melting points above 195° C. are obtained.

16 Claims, No Drawings

PROCESS FOR THE PREPARATION OF 4,4'-BIS(4-AMINOPHENOXY)-DIPHENYL SULFONE

BACKGROUND OF THE INVENTION

The invention relates to a new process for the sulfone from 4-aminophenol, alkali metal hydroxide and 4,4'-dihalodiphenyl sulfone in an organic solvent.

4,4'-Bis(4-aminophenoxy)diphenyl sulfone (BAPS) is an important monomer for the preparation of high-melting polyamides, polyamides and polyamidoimides. Furthermore, it is also suitable as a curing agent of epoxides.

According to DE-A-1,909,520, which is incorporated by reference herein in its entirety, BAPS is prepared from an alkali metal salt of p-aminophenol and a 4,4'-dihalodiphenylsulfone in a polar aprotic solvent, which can also be an N-alkylated acid amide, at 50° to 150° C. In this reaction, p-aminophenol and alkali metal hydroxide are used in equivalent amounts and the dihalo compound in a slightly less than equivalent amount, relative to the stoichiometrically required amount of p-amino-phenol. In the example, the molar ratio of p-aminophenol to 4,4'-dichlorodiphenyl sulfone is 2.063. The reaction is carried out in dimethyl sulfoxide at 100° C. The product is precipitated with water, dissolved, treated with activated carbon and reprecipitated. It then has a melting point of 191° to 192° C., which can be increased to 193° to 194° C. by recrystallization.

According to DE-A-2,315,607, which is incorporated by reference herein in its entirety, BAPS is prepared from p-aminophenol, sodium hydroxide and 4,4'-dichlorodiphenyl sulfone, stoichiometric amounts of the starting compounds being used. The reaction is carried out in dimethyl sulfoxide at 160° C. After two precipitations, a product having a melting point of 177° to 187°C. is obtained. After recrystallization, the melting point is 188° to 191° C.

According to Kawakami et al. (Journal of Polymer Science, Polymer Chemistry Edition, Vol. 12 (1974), 565-73), too, which is incorporated by reference herein in its entirety, BAPS is prepared from p-aminophenol, sodium hydroxide and 4,4'-dichlorodiphenyl sulfone in dimethyl sulfoxide. This article proposes a 1 to 2% molar excess of p-aminophenol, relative to sodium hydroxide. A sodium hydroxide excess is not recommended, since this can lead to the formation of nitrogen bridges. In a working example, the molar ratio of sodium hydroxide to p-aminophenol is 0.99 and that of p-aminophenol to 4,4'-dichlorodiphenyl sulfone is 2.10. This gives a product having a melting point of 189° to 191° C. After recrystallization, the melting point is 191° to 192° C.

For polycondensation purposes, very pure BAPS having a very high melting point is required. BAPS having a melting point below 191° C. is still unsuitable, while a product having a melting point of 191° to 193° C only leads to low-quality polycondensation products having a dark color and poor mechanical properties. The known processes thus provide a BAPS which is usable for polycondensations only after several purification steps and after recrystallization and often the BAPS provided is usable only to limited degree.

SUMMARY OF THE INVENTION

It is an object of the present invention to provide a simplified process for the preparation of BAPS of high purity. The product obtained after the completed reaction should be suitable for polycondensation purposes without recrystallization.

It is a further object of this invention to provide pristine (non-recrystallized) 4,4'-bis(4-amino phenoxy)-diphenyl sulfone of at least 99.0% purity from 4-aminophenol, an alkalimetal hydroxide and 4,4'-dihalodiphenyl sulfone.

Upon further study of the specification and appended claims, further objects and advantages of this invention will become apparent to those skilled in the art.

To attain these objects, there is provided a process for preparing 4,4'-bis(4-aminophenoxy)-diphenyl sulfone of high purity wherein 4-aminophenol is converted to the corresponding alkali metal phenolate, which is then reacted with 4,4'-dihalodiphenyl sulfone in an organic solvent, characterized in that:

1. 1.0 to 1.1 moles of alkali metal hydroxide are used per mole of 4-aminophenol to provide the alkali metal phenolate,
2. 2.005 to 2.05 moles of 4-aminophenol are used per mole of 4,4'-dihalodiphenyl sulfone, and
3. The organic solvent comprises a dialkylamide or N-alkyl lactam.

The alkali metal hydroxide is preferably used in a slightly excess of 1.01 to 1.05 mol per mole of 4-aminophenol. Sodium hydroxide or potassium hydroxide is preferably used as the alkali metal hydroxide. The alkali metal hydroxide is in general added in the form of an aqueous phase, 10 to 60% strength solutions being preferred. After the phenolate has been formed, the water is again removed. This can advantageously be carried out by axeotropic distillation with the aid of an organic solvent.

The molar ratio of 4-aminophenol to 4,4'-dihalo diphenyl sulfone is preferably 2.01 to 2.04. Suitable dihalo compounds include the dichloro and the dibromo compounds. 4,4'-dichlorodiphenyl sulfone is preferably used.

For the reaction of the alkali metal phenolate with the 4,4'-dihalodiphenyl sulfone, dialkylamides or N-alkyl lactams are suitable as solvent. Examples of these include but are not limited to dimethylformamide, dimethylacetamide, dimethylbenzamide, N-methylpyrrolidone, N-ethylpyrrolidone, N-methylpiperidone, N-methylcaprolactam and N-methyllauryllactam. N-methylpyrrolidone is the preferred solvent.

The reaction is preferably carried out in a 20 to 85% strength solution, relative to the phenolate and the dihalodiphenyl sulfone compound. The preferred reaction temperature is between 150° and 180° C., and the reaction is generally completed after 1 to 20 hours. In most cases, the reaction time is 2 to 10 hours.

The reaction of the alkali metal phenolate and the dihalo-compound can also be carried out in the presence of reducing agents, such as sodium hypophosphite or sodium dithionite. This avoids, in the case of non-quantitative exclusion of oxygen, the formation of quinones and a dark coloration of the product. Up to 5 mol % of reducing agent, relative to the dihalo-compound, is used.

BAPS is precipitated from the reaction solution by means of a precipitant. Suitable precipitants are mixtures of alcohol and water, hydrocarbon and water or hydrocarbon, alcohol and water. Alcohol/water mixtures are preferably used as precipitants. Suitable alcohols used in the precipitant mixtures are lower water-miscible alcohols, such as methanol, ethanol, isopropanol and n-propanol. Water-immiscible alcohols, such as, for example, butanol, hexanol or octanol can also be used. The precipitant mixtures can contain 10 to 90% of alcohol.

The process according to the invention produces a pristine BAPS which has a melting point above 193° C. without recrystallization. A surprisingly simple purification operation gives a BAPS which is at least 99.5% pure and has a melting point of at least 195° C. It can be used directly for the polycondensation of high-melting polymers of high molecular weight.

The procedure of the process according to the invention is in general carried out as follows:

4-Aminophenol is dissolved in a solvent mixture miscible with alkali metal hydroxide solution and consisting essentially of a dialkylamide or N-alkyl lactam and, for example, a hydrocarbon. Of these solvents, at least one should be capable of forming an azeotrope with water. Suitable hydrocarbons which form azeotropes with water are benzene, toluene, hexane, heptane, cyclohexane and the like. The solution is freed of oxygen by flushing with an inert gas, such as nitrogen or argon. A reducing agent can then be added to remove any traces of oxygen still present.

The aqueous alkali metal hydroxide solution is added to the solution of the 4-aminophenol at a temperature between room temperature and the boiling point of the hydrocarbon used. Once the formation of the phenolate is completed, the water is removed by azeotropic distillation.

A solution of the 4,4'-dihalodiphenyl sulfone in a dialkylamide or alkyl lactam is then added to the remaining solution of the aminophenolate in the dialkylamide (or N-alkyl lactam) and the hydrocarbon, the same dialkylamide or N-alkyl lactam preferably being used in both solutions. The reaction mixture is heated to the reaction temperature, as a result of which the hydrocarbon is distilled off.

After the reaction is completed, the reaction mixture is cooled to below 100° C., and the precipitant is added. The precipitated product is filtered off, washed with water, alcohol or a water/alcohol mixture and dried.

It is also advantageous if the reaction is conducted in any other solvent which does not interfere with the reaction. Consequently, a wide range of equivalent solvents are contemplated.

Likewise, it is advantageous to employ a single step of reacting an alkali metal 4-aminophenolate with 4,4'-dihalophenyl sulfone, using 2.005-2.05 moles of the former per mole of the latter.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

German application No. P 40 01 821.0, filed Jan. 23, 1990 is hereby incorporated by reference.

In the examples which follow, the examples according to the invention are denoted by numbers and the comparative examples by letters.

The melting points of BAPS given below were determined by the DSC method at a heating rate of 10° C./min.

The purity of the diamine was determined by thin-layer chromatography of silica gel with chloroform. Quantitative analysis of the result was carried out by UV spectroscopy.

EXAMPLE 1

42 g (1.05 mol) of NaOH (in the form of a 25% strength aqueous solution) were added at room temperature to a nitrogen-saturated solution of 109.5 g (1.0 mol) of 4-aminophenol in 100 ml of toluene and 100 ml of N-methylpyrrolidone. This solution is heated to an internal temperature of about 110° C., which initiates the distillation of the toluene/water azeotrope. The water is separated off by means of a water separator, and the toluene is recycled. After the water has been distilled off completely, the mixture is cooled to 60° C. At this temperature, a solution of 140.9 g (0.49 mol) of 4,4'-dichlorodiphenyl sulfone in 100 ml of N-methylpyrrolidone is added. The internal temperature is then continuously increased to 170° C. In the meantime, the toluene used is distilled off at an internal temperature of about 110° C. The temperature is maintained at 170° C. for 5 hours and then lowered to 70° C. At this temperature, 1.5 l of a water/methanol mixture (1:1) is slowly added, as a result of which the 4,4'-bis(4-aminophenoxy)diphenyl sulfone formed precipitates. The mixture is cooled to room temperature. The precipitated product is filtered off, washed with water and dried.

| Yield | 203.4 g = 96% of theory |
|---|---|
| Tm | 195.1° C. |
| Purity | 99.6% |

EXAMPLE 2 to 7 AND COMPARATIVE EXAMPLES A AND B

The procedure of Example 1 is repeated. The relative amounts and the conditions and results of the reactions are listed in Table 1.

TABLE 1

| | Molar ratio | | | | $Na_2S_2O_4$ | Reaction Temp. | Time | | Yield | $T_m$ | Purity |
|---|---|---|---|---|---|---|---|---|---|---|---|
| Ex. | DCDPS[1] | AP[2] | Base | Base | [mol %][3] | [°C.] | [h] | Precipitant | [%] | [°C.] | [%] |
| 1 | 1.0 | 2.041 | 2.143 | NaOH | — | 170 | 5 | $H_2O$/MeOH[4] | 96 | 195.1 | 99.6 |
| 2 | 1.0 | 2.009 | 2.01 | NaOH | — | 140 | 7 | $H_2O$/MeOH | 91 | 195.0 | 99.5 |
| 3 | 1.0 | 2.015 | 2.075 | NaOH | 1.0 | 140 | 10 | $H_2O$/EtOH[5] | 89 | 195.1 | 99.6 |
| 4 | 1.0 | 2.023 | 2.065 | KOH | 2.0 | 180 | 4 | $H_2O$/EtOH | 91 | 194.5 | 99.3 |
| 5 | 1.0 | 2.030 | 2.04 | KOH | — | 150 | 5 | $H_2O$/i-PrOH[6] | 93 | 195.8 | 99.9 |
| 6 | 1.0 | 2.038 | 2.10 | NaOH | — | 160 | 5 | $H_2O$/i-PrOH | 94 | 195.5 | 99.7 |
| 7 | 1.0 | 2.049 | 2.10 | NaOH | — | 170 | 5 | $H_2O$/MeOH | 96 | 195.1 | 99.6 |
| A | 1.0 | 2.0 | 2.0 | NaOH | — | 170 | 5 | $H_2O$/MeOH | 88 | 191.7 | 97.8 |

TABLE 1-continued

| Ex. | Molar ratio DCDPS[1] | AP[2] | Base | Base | Na₂S₂O₄ [mol %][3] | Reaction Temp. [°C.] | Time [h] | Precipitant | Yield [%] | T$_m$ [°C.] | Purity [%] |
|---|---|---|---|---|---|---|---|---|---|---|---|
| B | 1.0 | 2.1 | 2.05 | NaOH | — | 170 | 5 | H₂O/MeOH | 86 | 191.2 | 97.5 |

[1] 4,4'-Dichlorodiphenyl sulfone
[2] 4-Aminophenol
[3] relative to DCDPS
[4] Methanol
[5] Ethanol
[6] Isopropanol The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing 4,4'-bis(4-aminophenoxy)-diphenyl sulfone of high purity, comprising converting 4-aminophenol with an alkali metal hydroxide to the corresponding alkali metal phenolate, reacting resultant phenolate with a 4,4'-dihalodiphenyl sulfone in an organic solvent at 120° to 200°) C., precipitating the product with the aid of a precipitant, and separating resultant precipitated product, wherein, 1.0 to 1.1 moles of alkali metal hydroxide are used per mole of 4-aminophenol, 2.005 to 2.5 moles of 4-aminophenol are used per mole of 4,4'-dihalodiphenyl sulfone, and the organic solvent comprises a dialkylamide or N-alkyl lactam.

2. A process according to claim 1, wherein 1.01 to 1.05 moles of alkali metal hydroxide are used per mole of 4-aminophenol.

3. A process according to claim 1, wherein 2.01 to 2.04 mole of 4-aminophenol are used per mole of 4,4'-dihalodiphenyl sulfone.

4. A process according to claim 1, wherein the organic solvent comprises N-methylpyrrolidone.

5. A process according to claim 1, wherein the reaction is carried out in the presence of up to 5 mol % of a reducing agent, relative to 4,4'-dihalodiphenyl sulfone.

6. A process according to claim 1, wherein the alkali metal hydroxide is sodium hydroxide or potassium hydroxide.

7. A process according to claim 1, wherein 4,4'-dihalodiphenyl sulfone is 4,4'-dichlorodiphenyl sulfone.

8. A process according to claim 1, wherein the reaction of alkali metal phenolate with 4,4'-dihalodiphenyl sulfone is carried out at a temperature between 150° and 180° C.

9. A process according to claim 1, wherein the product is precipitated with the aid of an alcohol/water mixture.

10. A process as in claim 1, wherein the concentration of the phenolate and 4,4'-dihalodiphenyl sulfone in the organic solvent ranges from 20 to 85 wt. %.

11. A process as in claim 1, wherein the organic solvent additionally comprises a hydrocarbon solvent which forms an azeotrope with water.

12. A process according to claim 1, wherein the organic solvent comprises a dialkylamide or N-alkyl lactam of from 3 to 12 carbon atoms.

13. A process according to claim 1, wherein the organic solvent is dimethyl formamide, dimethyl acetamide, dimethyl benzamide, N-methyl pyrrolidone, N-ethylpyrrolidone, N-methyl piperidone, N-methyl capiolactam, or N-methyl lauryl lactam.

14. A process for preparing pristine 4,4 bis(4-aminophenoxy)-diphenyl sulfone of greater than 99.0% purity with a Tm greater than 195° C., wherein 4-aminophenol is converted with KOH or NaOH to the corresponding phenolate, which is reacted with a 4,4'-dichlorodiphenyl sulfone in an organic solvent at 150° to 180° C., the product is then precipitated by the addition of a water/alcohol mixture, wherein 1.01 to 1.05 moles of KOH or NaOH are used per mole of 4-aminophenol, 2.01 to 2.04 moles of 4-aminophenol are used per mole of 4,4'-dichlorodiphenyl sulfone, and N-methylpyrrolidone comprises the organic reaction solvent, with a concentration of from 20 to 85% 4-amino phenolate and 4,4'-dichloro diphenyl sulfone in the solvent, whereby the pristine sulfone is produced directly without crystallization.

15. A process as in claim 14, wherein the N-methyl pyrrolidone is used in admixture with toluene when forming the 4-amino phenolate.

16. A process for preparing a 4,4'-bis(4-aminophenoxy) diphenyl sulfone which comprises reacting an alkali metal 4-amino phenolate with 4,4'-dihalophenyl sulfone wherein 2.005–2.05 moles of the alkali metal 4-amino phenolate are used per mole of 4,4'-dihalodiphenyl sulfone.

* * * * *